United States Patent [19]

Anzalone

[11] Patent Number: 4,810,696
[45] Date of Patent: Mar. 7, 1989

[54] DIETHYLAMINOETHYL DEXTRAN FOR DECREASING HYPERGLYCEMIA

[75] Inventor: Sergio Anzalone, Albano Laziale, Italy

[73] Assignee: Medosan Indusrie Biochemiche Riunite S.p.A, Rome, Italy

[21] Appl. No.: 66,452

[22] Filed: Jun. 26, 1987

[30] Foreign Application Priority Data

Aug. 1, 1986 [IT] Italy .................... 48345 A/86

[51] Int. Cl.$^4$ .................... A61K 31/73; C08B 37/02
[52] U.S. Cl. .................... 514/59; 514/866; 536/51
[58] Field of Search .................... 514/59, 866; 536/51

[56] References Cited

U.S. PATENT DOCUMENTS 3,624,209 11/1971 Granatek et al. .................... 514/59
3,851,057 11/1974 Kuzuya .................... 536/51
4,160,826 7/1979 Fischetti .................... 514/59
4,562,178 12/1985 Vita .................... 514/59

FOREIGN PATENT DOCUMENTS 0066135 12/1982 European Pat. Off. .................... 536/51
3447735 6/1985 Fed. Rep. of Germany .................... 514/59
61-64701 4/1986 Japan .................... 514/59

OTHER PUBLICATIONS

Parkinson; Nature, 215:415–416, (1967).

*Primary Examiner*—Ronald W. Griffin
*Assistant Examiner*—Nancy S. Carson
*Attorney, Agent, or Firm*—Cushman, Darby & Cushman

[57] ABSTRACT

Diethylaminoethyl dextran (DEAE-D) has an activity for decreasing hyperglycemia, leading to an improved balance of the glucosic metabolism and can be usefully administered to diabetics.

3 Claims, No Drawings

DIETHYLAMINOETHYL DEXTRAN FOR DECREASING HYPERGLYCEMIA

BACKGROUND OF THE INVENTION

1. Field of the invention

The present invention relates to a novel pharmaceutical utilization of diethylaminoethyl dextran (DEAE-D) in a treatment for decreasing hyperglycemia in subjects suffering from a high glucidic level in blood.

The use of DEAE-D is particularly advantageous for diabetic patients.

2. Description of the prior art

DEAE-D is a well known substance which has found therapeutic utility for its antisteatogenous and hypolipidemizing activity at the intestinal level, as described in U.S. Pat. No. 4,160,826.

More recently it was discovered that DEAE-D in an acute administration is useful for decreasing the post prandial hyperinsulinemia.

As described in U.S. Pat No. 4,562,178, DEAE-D can be used for treating patients suffering from hypoglycemia caused by some form of hyperinsulinemia, in order to lower the insulin level and to raise the glucidic level in blood.

It has now suprisingly been found that DEAE-D can also be used therapeutically for a completely reversed utilization, namely for lowering the glucidic level in blood.

This fact is the more suprising, as the teaching of the prior art was leading to deny any interference of the substance in decreasing the glucosic metabolism. In fact the utility in endogenous and reactive hypoglycemia would not imply that DEAE-D could also be active in hyperglycemia.

In fact it appears now that DEAE-D has a controlling activity on an altered glucosic metabolism, which is the more unexpected as there is no other substance known which could effect such a double action, in an apparently counteracting manner.

Substances are known, in fact, which show either only a hypoglycemizing activity, such as sulphonylureas, or only a hyperglycemizing activity, such as glucagone.

SUMMARY OF THE INVENTION

An object of the present invention is the use of DEAE-D as an active substance for lowering an increased glucidic level in blood caused by an altered glucosic metabolism.

The invention is particularly useful in patients affected with diabetes in its more or less severe forms.

It has been assessed that DEAE-D, when administered orally, carries out a marked activity in lowering the hematic glucose concentration and this activity in time leads to a considerable increase of hemoglobin glucosylate.

As it is well known, diabetic patients are clinically classified under three types: type 1 is insulin dependant, type 2 is affected with alimentary diabetes and type 3 is affected with glucidic intolerance.

In all types of diabetics, DEAE-D lowers the glycemic concentration, improves the basic glucose metabolism and reduces the need for insulin.

The active substance is administered orally in the form of capsules, powder and the like together with a pharmaceutically acceptable inert eccipient or, depending on the needs of the patient, with additional compatible drugs.

The dosage has to be suited to the needs of the patient, however in general the daily dose is from 1,5 to 5 g. of DEAE-D, preferably 1.5 to 3 g. per day.

Results of tests are reported in the following.

PRELIMINARY TESTS

A study on DEAE-D has been carried out to verify whether the parameters of glycemia could be involved in a group of 35 obese children and it was observed that DEAE-D reduced glycemia significantly both when induced by a standard meal and an oral glucose load.

The results of glycemia value are referred in Tables I and II.

TABLE I

Values of glycemia after standard meal without (G) and with ($G_1$) administration of DEAE-D

| SUBJECT N° | | BASAL | TIME (Minutes) | | | | | |
|---|---|---|---|---|---|---|---|---|
| | | | 30 | 60 | 90 | 120 | 150 | 180 |
| 1 | G | 80 | 121 | 113 | 123 | 105 | 102 | 99 |
| | $G_1$ | 82 | 111 | 101 | 116 | 125 | 110 | 90 |
| 2 | G | 86 | 118 | 95 | 106 | 105 | 100 | 94 |
| | $G_1$ | 85 | 87 | 131 | 113 | 117 | 98 | 88 |
| 3 | G | 76 | 134 | 117 | 107 | 116 | 112 | 98 |
| | $G_1$ | 75 | 120 | 105 | 98 | 100 | 92 | 84 |
| 4 | G | 75 | 120 | 99 | 97 | 95 | 100 | 83 |
| | $G_1$ | 85 | 119 | 95 | 99 | 94 | 96 | 77 |
| 5 | G | 86 | 103 | 126 | 103 | 111 | 97 | 88 |
| | $G_1$ | 85 | 106 | 127 | 115 | 112 | 93 | 80 |
| 6 | G | 84 | 108 | 134 | 130 | 93 | 114 | 99 |
| | $G_1$ | 80 | 89 | 118 | 115 | 102 | 97 | 85 |
| 7 | G | 97 | 147 | 160 | 134 | 135 | 125 | 118 |
| | $G_1$ | 88 | 104 | 135 | 133 | 123 | 110 | 102 |
| 8 | G | 93 | 176 | 193 | 167 | 148 | 127 | 114 |
| | $G_1$ | 88 | 124 | 123 | 114 | 124 | 110 | 99 |
| 9 | G | 94 | 181 | 167 | 168 | 145 | 133 | 118 |
| | $G_1$ | 85 | 149 | 142 | 200 | 101 | 92 | 86 |
| 10 | G | 85 | 115 | 90 | 102 | 90 | 100 | 88 |
| | $G_1$ | 80 | 102 | 90 | 95 | 85 | 100 | 86 |
| 11 | G | 85 | 102 | 130 | 100 | 90 | 93 | — |
| | $G_1$ | 85 | 95 | 110 | 100 | 88 | 82 | — |
| 12 | G | 95 | 120 | 115 | 105 | 78 | 90 | 70 |
| | $G_1$ | 90 | 102 | 95 | 88 | 78 | 85 | 80 |
| 13 | G | 84 | 128 | 134 | 120 | 95 | 100 | 105 |
| | $G_1$ | 80 | 100 | 95 | 98 | 80 | 85 | 79 |
| 14 | G | 70 | 130 | 105 | 90 | 95 | 90 | — |
| | $G_1$ | 80 | 102 | 90 | 70 | 95 | 80 | — |
| 15 | G | 92 | 150 | 145 | 160 | 130 | 104 | — |
| | $G_1$ | 80 | 120 | 140 | 155 | 102 | 95 | — |

TABLE II

Values of glycemia during OGTT without (G) and with ($G_1$) administration of DEAE-D

| SUBJECT N° | | BASAL | TIME (Minutes) | | | | | |
|---|---|---|---|---|---|---|---|---|
| | | | 30 | 60 | 90 | 120 | 150 | 180 |
| 1 | G | 76 | 112 | 111 | 102 | 112 | 104 | 109 |
| | $G_1$ | 74 | 121 | 119 | 107 | 98 | 113 | 101 |
| 2 | G | 85 | 160 | 130 | 112 | 115 | 86 | 100 |
| | $G_1$ | 88 | 134 | 115 | 132 | 119 | 106 | 102 |
| 3 | G | 87 | 141 | 145 | 103 | 123 | 99 | 92 |
| | $G_1$ | 76 | 126 | 119 | 104 | 117 | 94 | 80 |
| 4 | G | 73 | 164 | 102 | 106 | 102 | 96 | 92 |
| | $G_1$ | 96 | 145 | 98 | 104 | 100 | 95 | 95 |
| 5 | G | 79 | 109 | 107 | 97 | 93 | 96 | 96 |
| | $G_1$ | 63 | 99 | 109 | 99 | 99 | 96 | 98 |
| 6 | G | 86 | 156 | 138 | 144 | 125 | 132 | 124 |
| | $G_1$ | 96 | 124 | 147 | 154 | 157 | 120 | 122 |
| 7 | G | 88 | 125 | 121 | 114 | 102 | 110 | 111 |
| | $G_1$ | 95 | 131 | 91 | 110 | 122 | 114 | 99 |
| 8 | G | 91 | 176 | 180 | 161 | 139 | 113 | 128 |
| | $G_1$ | 84 | 162 | 129 | 115 | 126 | 103 | 105 |
| 9 | G | 92 | 126 | 119 | 133 | 117 | 111 | 101 |
| | $G_1$ | 95 | 105 | 94 | 127 | 115 | 125 | 103 |
| 10 | G | 86 | 141 | 160 | 158 | 118 | 108 | 122 |

TABLE II-continued

Values of glycemia during OGTT without (G) and with (G₁) administration of DEAE-D

| SUB-JECT N° | | BASAL | 30 | 60 | 90 | 120 | 150 | 180 |
|---|---|---|---|---|---|---|---|---|
| | $G_1$ | 87 | 100 | 139 | 152 | 137 | 117 | 112 |
| 11 | G | 83 | 166 | 140 | 115 | 120 | 121 | 112 |
| | $G_1$ | 86 | 148 | 119 | 121 | 122 | 118 | 107 |
| 12 | G | 74 | 130 | 158 | 144 | 117 | 138 | 126 |
| | $G_1$ | 73 | 116 | 108 | 95 | 114 | 119 | 99 |
| 13 | G | 96 | 143 | 154 | 141 | 116 | 120 | 122 |
| | $G_1$ | 91 | 112 | 141 | 123 | 109 | 115 | 106 |
| 14 | G | 85 | 148 | 142 | 102 | 115 | 90 | 88 |
| | $G_1$ | 79 | 120 | 115 | 100 | 107 | 85 | 78 |
| 15 | G | 80 | 165 | 128 | 115 | 118 | 90 | 98 |
| | $G_1$ | 82 | 152 | 100 | 131 | 120 | 95 | 100 |
| 16 | G | 76 | 127 | 145 | 138 | 120 | 135 | 120 |
| | $G_1$ | 78 | 112 | 110 | 90 | 106 | 102 | 93 |
| 17 | G | 88 | 122 | 158 | 134 | 125 | 135 | 120 |
| | $G_1$ | 85 | 110 | 100 | 94 | 105 | 105 | 100 |
| 18 | G | 110 | 154 | 88 | 130 | 90 | 70 | 80 |
| | $G_1$ | 85 | 110 | 100 | 122 | 85 | 80 | 92 |
| 19 | G | 82 | 96 | 126 | 140 | 140 | 115 | 125 |
| | $G_1$ | 79 | 102 | 138 | 135 | 142 | 120 | 119 |
| 20 | G | 95 | 140 | 158 | 145 | 120 | 116 | 125 |
| | $G_1$ | 92 | 115 | 116 | 125 | 108 | 110 | 105 |

Nine patients have then been selected which, subjected to a glucidic load per os (OGTT=75 g. glucose) showed alteration of the glycemic diagram. Said patients, ageing from 23 to 61, hospitalized for cardio-vascular or so alleged pathologies, were subjected to a hyposodic normocaloric diet.

Samples for the glycemic diagrams were taken in the morning at fasting and after a glucose load per os of 75 g., at zero, 30, 60, 90, 120, 180 minutes.

After 3 to 5 days the glycemic diagram was repeated on administering DEAE-D simultaneously to the glucidic load.

After evaluating the results statistically, by calculation of variance and covariance, a significant decrease of the glycemic values was observed.

The results are referred in Table III.

TABLE III

| SUBJECT | | BASAL | 30 | 60 | 90 | 120 | 180 |
|---|---|---|---|---|---|---|---|
| (1) | A | 0.94 | 2.20 | 2.30 | 2.70 | 1.98 | 0.88 |
| | B | 0.90 | 1.90 | 2.40 | 2.19 | 1.69 | 0.62 |
| (2) | A | 0.67 | 0.99 | 1.44 | 1.67 | 1.26 | 0.94 |
| | B | 0.55 | 1.07 | 1.11 | 1.19 | 1.03 | 0.93 |
| (3) | A | 0.53 | 1.14 | 1.22 | 0.88 | 0.74 | 0.60 |
| | B | 0.59 | 1.24 | 0.94 | 0.61 | 0.65 | 0.80 |
| (4) | A | 0.75 | 1.05 | 1.24 | 1.44 | 1.13 | 1.02 |
| | B | 0.59 | 1.17 | 1.10 | 1.00 | 0.83 | 0.69 |
| (5) | A | 0.53 | 1.50 | 1.96 | 2.12 | 1.91 | 0.99 |
| | B | 0.77 | 1.10 | — | 1.13 | 0.88 | — |
| (6) | A | 0.83 | 1.12 | 1.48 | 1.95 | 2.39 | 1.99 |
| | B | 0.88 | 1.35 | 1.60 | 1.93 | 1.47 | 1.30 |
| (7) | A | 0.71 | 1.29 | 1.77 | 2.38 | 2.00 | 1.18 |
| | B | 0.86 | 1.49 | 1.63 | 1.62 | 1.32 | 0.74 |
| (8) | A | 1.25 | 1.53 | 1.97 | 2.23 | 2.10 | 1.69 |
| | B | 0.91 | 1.28 | 1.56 | 1.89 | 1.79 | 1.74 |
| (9) | A | 0.68 | 1.27 | 1.48 | 1.85 | 1.81 | 1.31 |
| | B | 0.61 | 1.10 | 1.17 | 1.57 | 0.70 | 0.71 |

A = glycemic diagram after glucose load
B = glycemic diagram after glucidic load plus DEAE-D In view of these suprising results, the activity of DEAE-D was verified directly on patients affected with type 2 diabetes, in treatments both with sole diet and with diet plus oral hypoglycemizing drugs.

CLINICAL TESTS

Materials and Methods

Twenty nine patients affected with type 2 diabetes have been examined. Ten of them were treated with sole diet and 19 with diet plus oral hypoglycemizing drugs (OHA). As hypoglycemizing drugs sulphanylureas and biguanides have been used.

The OHA group in turn was divided into two subgroups:

in the first sub-group (10 patients) DEAE-D was added to OHA;

in the second sub-group (9 patients) DEAE-D only was used in substitution of OHA.

The metabolic examination was effected by the breakfast test (200 g. milk plus 50 g. bread) carried out in the morning with no administration of DEAE-D first, and seven days and thirty days after administration of this drug. To all the examined subjects 1 g. of the drug was administered immediately before the load test. Blood samples for measuring glycemia and insulinemia (IRI) were made after 0, 60, 90, 120 and 180 minutes from the loading time. To the diabetics previously treated with sole diet and the OHA plus DEAE-D group 1,5 g. of the drug under test were administered daily (breakfast, lunch and dinner), whereas to the group in which OHA was completely substituted with DEAE-D, 3 g/day (3x1 g/day) were administered.

Basally and after one month of treatment, in addition to glycemia and IRI induced by the load test, hemoglobin glucosylate and the weight were examined.

Statistical analysis was effected by resorting to the "t" Student test for paired and non paired data. The results are referred in Tables IV, V, VI.

TABLE IV

Glycemia values during BTT, before, after 7 days and after 30 days combined treatment with DEAE-D

| TIME OF TEST | BTT: GLYCEMIA mg % | | | | |
|---|---|---|---|---|---|
| | 0 | 60 | 90 | 120 | 180 |
| DIET + 1.5 g DEAE-D (10 observations) | | | | | |
| BASAL | 139 ± 10 | 219 ± 9 | 218 ± 13 | 207 ± 16 | 170 ± 12 |
| 7 DAYS | 132 ± 7 | 201 ± 9 | 206 ± 8 | 192 ± 9 | 149 ± 9 |
| 30 DAYS | 106 ± 3** | 165** ± 10*** | 172** ± 10*** | 144** ± 15*** | 115** ± 12*** |
| OHA + 1.5 g DEAE-D (10 observations) | | | | | |
| BASAL | 187 ± 13 | 265 ± 18 | 283 ± 19 | 276 ± 19 | 243 ± 18 |
| 7 DAYS | 161 ± 12* | 235 ± 15* | 258 ± 14* | 239 ± 14* | 199 ± 15* |
| 30 DAYS | 175 ± 23 | 244 ± 24 | 241 ± 27 | 226 ± 30 | 192 ± 27** |
| Substitution of OHA with 3 g DEAE-D (9 observations) | | | | | |
| BASAL | 157 ± 17 | 211 ± 20 | 239 ± 14 | 235 ± 13 | 219 ± 13 |
| 7 DAYS | 151 ± 11* | 180 ± 15* | 216 ± 13* | 210 ± 8* | 195 ± 8* |

TABLE IV-continued

Glycemia values during BTT, before, after 7 days and after 30 days combined treatment with DEAE-D

| TIME OF TEST | BTT: GLYCEMIA mg % | | | | |
|---|---|---|---|---|---|
| | 0 | 60 | 90 | 120 | 180 |
| 30 DAYS | 152 ± 18 | 194 ± 20 | 223 ± 17 | 209 ± 19** | 192 ± 13** |
| DIET + OHA + 1.5 g/die DEAE-D (9 observations) | | | | | |
| BASAL | 164 ± 10 | 243 ± 11 | 252 ± 14 | 244 ± 14 | 201 ± 14 |
| 7 DAYS | 147 ± 8* | 219 ± 9* | 233 ± 10* | 217 ± 10* | 175 ± 11* |
| 30 DAYS | 144 ± 16 | 208 ± 17** | 209 ± 18** | 188** ± 21*** | 157** ± 19*** |

Significance:
*Basal vs 7
**Basal vs 30
***7 vs 30

TABLE V

Values of basal insulinemia (IRI) as a response to BTT, before and after association (diet/OHA) with DEAE-D

| TIME OF TEST | BTT: IRI uU/ml | | | | |
|---|---|---|---|---|---|
| | 0 | 60 | 90 | 120 | 180 |
| Global group (29 observations) | | | | | |
| BASAL | 13 ± 4 | 40 ± 7 | 47 ± 7 | 44 ± 12 | 29 ± 7 |
| 7 DAYS | 13 ± 3 | 40 ± 10 | 50 ± 9 | 53 ± 11 | 32 ± 8 |
| 30 DAYS | 14 ± 3 | 39 ± 5 | 46 ± 10 | 43 ± 9 | 24 ± 6 |
| DIET + DEAE-D (10 observations) | | | | | |
| BASAL | 13 ± 5 | 51 ± 10 | 59 ± 15 | 33 ± 7 | 26 ± 8 |
| 7 DAYS | 16 ± 5 | 59 ± 11 | 51 ± 10 | 56 ± 19 | 25 ± 7 |
| 30 DAYS | 14 ± 7 | 73 ± 19 | 59 ± 11 | 61 ± 15 | 21 ± 8 |
| OHA + 1.5 and 3 g DEAE-D groups (19 observations) | | | | | |
| BASAL | 17 ± 5 | 36 ± 9 | 44 ± 10 | 51 ± 19 | 29 ± 11 |
| 7 DAYS | 15 ± 4 | 37 ± 10 | 45 ± 12 | 52 ± 14 | 37 ± 12 |
| 30 DAYS | 14 ± 4 | 33 ± 6 | 29 ± 6 | 32 ± 9 | 26 ± 9 |

TABLE VI

Variations of hemoglobin glucosylate (HbA$_1$C) following 30 days combined treatment with DEAE-D
TOTAL OF OBSERVATIONS (29)

| TIME OF TEST | HbA$_1$C (%) |
|---|---|
| BASAL | 8.32 ± 0.48 |
| 30 DAYS | 7.87 ± 0.42 |
| p< | 0.001 |
| DIET + DEAE-D (10 observations) | |
| BASAL | 7.85 ± 0.34 |
| 30 DAYS | 6.98 ± 0.31 |
| p< | 0.001 |
| OHA + DEAE-D groups (19 observations) | |
| BASAL | 9.02 ± 0.73 |
| 30 DAYS | 8.73 ± 0.76 |
| p< | 0.025 |

RESULTS (A1) Breakfast Test (glycemia)

(a) Diet plus 1.5 g. DEAE-D. As it is possible to observe in Table IV, glycemia was progressively and significantly reduced after one week and thirty days from administration of the drug. The following significances are observed:
on time 0 of BTT: $p<0.025$ basal examination versus 30 days;
on time 60 minutes: $p<0.001$ basal versus 30 days and $p<0.05$ 7 days versus 30 days;
on time 90 minutes: $p<0.05$ basal versus 30 days and $p<0.025$ 7 and 30 days;
on time 120 minutes: $p<0.0125$ basal versus 30 days and $p<0.01$ seven days versus 30 days;
on time 180 minutes: $p<0.01$ basal versus 30 days, $p<0.05$ 7 days versus 30 days and $p<0.0125$ basal versus 7 days.

(b) OHA plus 1.5 g DEAE-D. As referred in Table IV, in this group again glycemia was reduced after administration of DEAE-D. In this group the following significances were observed.
on time 0 of BTT: $p<0.0125$ basal examination versus 7 days;
on time 60 minutes: $p<0.01$ basal versus 7 days;
on time 90 minutes: $p<0.0125$ basal versus 7 days;
on time 120 minutes: $p<0.01$ basal versus 7 days;
on time 180 minutes: $p<0.01$ basal versus 7 days and $p<0.0125$ basal versus 30 days.

(c) OHA substituted with 3 g DEAE-D. As referred in Table IV, by substituting OHA with 3 g DEAE-D not only was the metabolic control not worsened, but it was improved as evidenced by different significant decreases:
on time 0 of BTT: $p<0.05$ basal versus 7 days;
on time 60 minutes: $p<0.0125$ basal versus 7 days;
on time 90 minutes: $p<0.05$ basal versus 7 days;
on time 120 minutes: $p<0.01$ basal versus 7 days and $p<0.05$ basal versus 30 days;
on time 180 minutes: $p<0.01$ basal versus 7 days and $p<0.05$ basal versus 30 days.

(d) On the last diagram of Table IV the examination carried
out with 1.5 g DEAE-D is reported globally (group with diet plus oral hypoglycemizing drugs). As can be noted, the significancies were still more evidenced, probably due to an increased number of observations.

(A2) Breakfast Test (insulinemia - IRI)

As can be noted from Table V the IRI values both basal and induced by BTT show little variation in the groups as globally considered, even when, on analysing the individual examined groups, it is noted that in the patients treated with OHA plus DEAE-D a certain decrease of IRI at various times of BTT was observed.

The above can be explained in that the drug has not an insulin mediator activity as the other hypoglycemizing drugs do (for example sulphanylureas); consequently on reducing the hematic glucose concentration during the treatment, the beta-insular secretion already prejudiced in some types of diabetes, is reduced by having to face a reduced metabolic load.

(B) Hemoglobin glucosylate (HbA$_1$C)

Following 30 days of combined therapy consisting of diet plus DEAE-D or OHA plus DEAE-D a marked and significant improvement of the metabolic control is observed considering the examined cases both globally and individually. The results are referred in Table VI.

(C) Weight

As far as the weight is concerned no significant variations are observed after 30 days of combined therapy in the different groups. In fact, globally, in the patients under test the weight was 75.64±2.85 Kg before test and 75.5±2.76 Kg after 30 days of combined therapy.

I claim:

1. A method for decreasing hyperglycemia in humans comprising administering orally to a hyperglycemic subject an amount of Diethylaminoethyl dextran pharmaceutically effective to decrease the level of glycemia.

2. The method of claim 1 for the treatment of hyperglycemia in subjects suffering from diabetes.

3. The method of claim 1 for the treatment of hyperglycemia in subjects suffering from alimentary diabetes.

* * * * *